(12) United States Patent
Saltiel

(10) Patent No.: US 6,458,151 B1
(45) Date of Patent: Oct. 1, 2002

(54) OSTIAL STENT POSITIONING DEVICE AND METHOD

(76) Inventor: Frank S. Saltiel, 6330 Briar Rd., Willowbrook, IL (US) 60521

(*) Notice: Subject to any disclaimer, the term of this patent is extended or adjusted under 35 U.S.C. 154(b) by 125 days.

(21) Appl. No.: 09/656,886

(22) Filed: Sep. 7, 2000

Related U.S. Application Data

(60) Provisional application No. 60/153,037, filed on Sep. 10, 1999.

(51) Int. Cl.$^7$ .................................................. A61F 2/06
(52) U.S. Cl. ................. 623/1.11; 604/104; 604/164.01; 606/195; 606/194; 606/198
(58) Field of Search ................................ 606/191–192, 606/194–195, 198, 108, 1, 200, 151; 623/1.11, 12.11, 66.1; 604/104, 96.01, 105–106, 508, 171, 103.1, 264, 523, 529, 103.5, 164.01; 128/898

(56) References Cited

U.S. PATENT DOCUMENTS

| | | | |
|---|---|---|---|
| 5,607,444 A | 3/1997 | Lam | 606/194 |
| 5,607,466 A | 3/1997 | Imbert et al. | 623/1 |
| 5,617,878 A | 4/1997 | Taheri | 128/898 |
| 5,632,762 A * | 5/1997 | Myler | 606/192 |
| 5,749,825 A | 5/1998 | Fischell et al. | 600/3 |
| 5,749,890 A | 5/1998 | Shaknovich | 606/198 |
| 5,868,777 A | 2/1999 | Lam | 606/194 |
| 5,910,154 A * | 6/1999 | Tsugita et al. | 606/200 |
| 6,096,071 A * | 8/2000 | Yadav | 606/194 |
| 6,143,021 A | 11/2000 | Staehle | 623/1.11 |
| 6,171,328 B1 * | 1/2001 | Addis | 606/200 |
| 6,290,710 B1 * | 9/2001 | Cryer et al. | 606/159 |
| 6,334,864 B1 | 1/2002 | Amplatz | 606/200 |

* cited by examiner

Primary Examiner—David J. Isabella
Assistant Examiner—Urmi Chattopadhyay
(74) Attorney, Agent, or Firm—Crompton, Seager & Tufte, LLC

(57) ABSTRACT

A stent positioning device and associated method for precisely delivering and deploying an intravascular stent in a vascular lumen adjacent the ostium thereof. The stent positioning device is slidably disposed about a stent delivery catheter and includes a distally disposed expandable member having an expanded diameter that is larger than the vascular lumen adjacent the ostium. The stent positioning device is positioned in the vasculature such that the distal end of the expandable member engages the ostium. The stent delivery catheter is positioned such that the proximal end of the stent is positioned adjacent the distal end of the expandable member by using either a visible marker on the stent delivery catheter or a radiopaque marker on the expandable member. When the stent is positioned adjacent the distal end of the expandable member, the stent may be deployed such that the proximal end of the stent is located in the vascular lumen adjacent the ostium.

26 Claims, 3 Drawing Sheets

OSTIAL STENT POSITIONING DEVICE AND METHOD

RELATED APPLICATIONS

This application claims priority to U.S. Provisional Patent Application No. 60/153,037, filed Sep. 10, 1999, entitled AORTO-OSTLAL STENT LOCATOR, the entire disclosure of which is hereby incorporated by reference.

FIELD OF THE INVENTION

The present invention generally relates to intravascular devices. More specifically, the present invention relates to intravascular stent delivery catheters and methods of use.

BACKGROUND OF THE INVENTION

Intravascular stents are commonly used to maintain patency of a vascular lumen, particularly after an angioplasty (e.g., PTCA or PTA) or an atherectomy procedure. Intravascular stents come in a wide variety of designs, but typically comprise a metallic expandable structure, and are usually either self-expanding or balloon-expandable. Intravascular stents are typically delivered and deployed utilizing a stent delivery catheter such as a balloon catheter. The stent delivery catheter is advanced over a guidewire through a guide catheter, and with the assistance of radiographic fluoroscopy, is navigated to the desired treatment site.

In most instances, the desired treatment site is located well within a vascular lumen distal of the corresponding ostium. In other instances, the treatment site is located in the vascular lumen immediately adjacent the ostium. For example, in coronary applications, the treatment site may be located in the right coronary artery (RCA) immediately adjacent the ostium in the aortic wall. In such instances, it is often difficult to precisely position the intravascular stent such that the stent is completely within the vascular lumen and as close as possible to the ostium. In other words, it is very difficult using conventional radiographic fluoroscopic techniques to position the stent in the vascular lumen adjacent the ostium without having a portion of the stent extending proximal of the ostium.

If any portion of the intravascular stent is placed proximal of the ostium, the protruding portion of the stent may initiate a thrombogenic response potentially creating a distal embolism. For example, in coronary applications, a stent protruding into the lumen of the ascending aorta may cause an embolism to form in the cerebral vasculature potentially resulting in a stroke. Accordingly, because of the limitations associated with conventional stent delivery catheters and radiographic fluoroscopic visualization techniques, there is a substantial unmet need for an improved device and method for precisely positioning an intravascular stent in a vascular lumen adjacent the corresponding ostium.

SUMMARY OF THE INVENTION

To satisfy this substantial unmet need, the present invention provides a stent positioning device and associated method for precisely delivering and deploying an intravascular stent in a vascular lumen adjacent the ostium thereof. The present invention may be utilized for both coronary and peripheral vascular applications. The stent positioning device is slidably disposed about a stent delivery catheter and includes a distally disposed expandable member having an expanded diameter that is larger than the vascular lumen adjacent the ostium. The stent positioning device is positioned in the vasculature such that the distal end of the expandable member engages the ostium. The stent delivery catheter is positioned such that the proximal end of the stent is positioned adjacent the distal end of the expandable member by using either a visible marker on the stent delivery catheter or a radiopaque marker on the expandable member. When the proximal end of the stent is positioned adjacent the distal end of the expandable member, the stent may be deployed such that the proximal end of the stent is precisely located in the vascular lumen adjacent the ostium.

In the visible marker embodiment, the stent delivery catheter includes a visible marker disposed on the proximal portion of the shaft. The proximal visible marker is separated from the proximal end of the distally disposed stent by a length equal to the overall length of the stent positioning device. With this arrangement, the proximal end of the stent may be precisely located in the vascular lumen adjacent the ostium when the proximal end of the stent positioning device is located at the visible marker and the distal end of the expandable member engages the ostium.

In the radiopaque expandable member embodiment, the distal end of the expandable member is radiopaque or includes a radiopaque marker disposed thereon. The proximal end of the stent may be precisely located in the vascular lumen adjacent the ostium by utilizing radiographic techniques to position the proximal end of the stent at the distal end of the expandable member when the distal end of the expandable member engages the ostium.

In a preferred embodiment, the present invention provides a method including the initial step of placing the stent positioning device about the stent delivery catheter, which may be performed by the physician or by the manufacturer of the stent delivery catheter. The stent delivery catheter with the stent disposed thereon is inserted and navigated through the vasculature, across the ostium and into the vascular lumen to be treated, with the distal end of the expandable member disposed proximal of the ostium. The expandable member is then expanded and advanced until the distal end thereof engages the ostium. The stent delivery catheter is then retracted in the proximal direction until the proximal end of the stent is positioned adjacent the distal end of the expandable member. This may be accomplished by utilizing a visible marker on the proximal portion of the stent delivery catheter as described previously. Alternatively, this may be accomplished by providing a radiopaque distal end on the expandable member and using radiographic visualization techniques. The stent may then be deployed such that the proximal end of the stent is located in the vascular lumen immediately adjacent the ostium.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
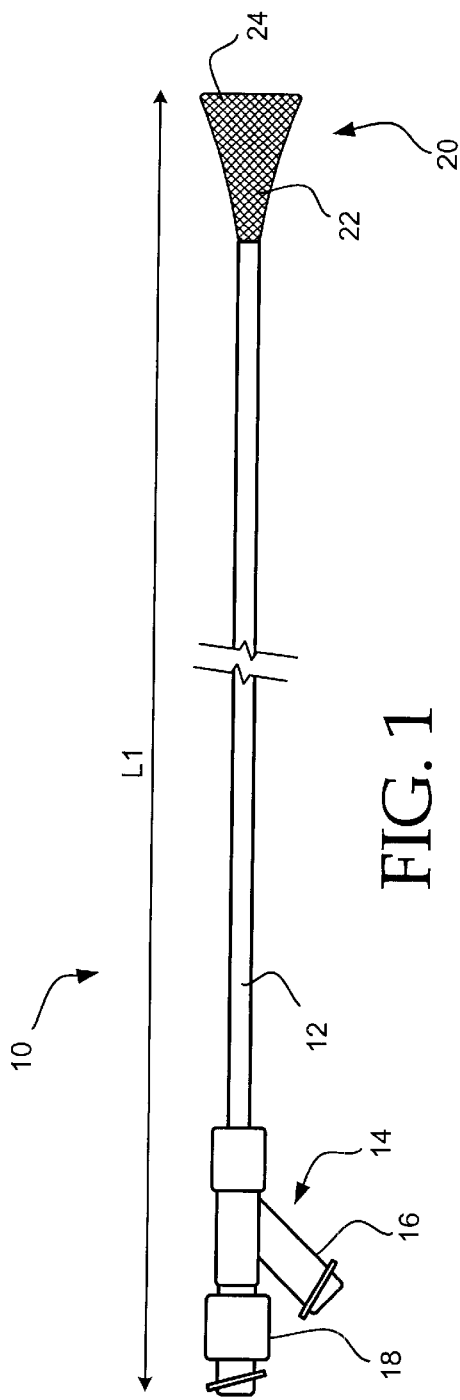
FIG. 1 is a schematic illustration of a stent positioning device in accordance with the present invention.

Refer now to FIG. 1 which is a schematic illustration of a stent positioning device 10 in accordance with the present invention. The stent positioning device 10 includes an elongate shaft 12 having a proximal end and a distal end and a lumen (not shown) extending therethrough. A manifold 14 is connected to the proximal end of the shaft 12, and an expandable member 20 is connected to the distal end of the shaft 12. The stent positioning device 10, including the manifold 14, the elongate shaft 12 and the expandable member 20, has an overall length L1.

The elongate shaft 12 may comprise a conventional catheter shaft design, and preferably includes a relatively stiff proximal section (e.g., metallic hypotube or braid composite) and a relatively flexible distal section (e.g., polymer extrusion). Also preferably, the entire length of elongate shaft 12 is longitudinally rigid such that longitudinal elongation and compression are minimized.

The manifold 14 includes a sidearm 16 and a rotational hemostasis valve 18. The sidearm 16 of the manifold 14 is in fluid communication with the lumen of the elongate shaft 12 to facilitate flushing of the lumen with heparinized saline, contrast media or the like. The rotatable hemostasis valve 18 provides access to the lumen of the shaft 12 such that other intravascular devices may be inserted therein. The rotational hemostasis valve 18 provides a fluid tight seal about such devices, and also provides a mechanical lock onto such devices thereby limiting relative movement therebetween.

The expandable member 20 preferably comprises a radially resilient but longitudinally rigid body 22. The body 22 of the expandable member 20 is preferably radially resilient in order to facilitate elastic expansion and collapse. The body 22 is also preferably longitudinally rigid such that the overall length of the stent positioning device 10 does not change when the distal end 24 of the expandable member 20 engages the ostium as will be described in more detail hereinafter. The body 22 of the expandable member 20 preferably includes perfusion holes or apertures to facilitate blood perfusion across the expandable member 20 and into the ostium and vascular lumen.

Also preferably, the body 22 of the expandable member 20 is self-expanding such that the expandable member 20 is in an expanded/deployed position (shown) when in a relaxed state. The body 22 may comprise a tubular braid or mesh formed of a super elastic material such as a nickel titanium alloy. The super elastic nature of the body 22 provides the self-expanding property. Alternatively, the expandable member 20 may include a super elastic hoop at the distal end 24 thereof. In this alternative embodiment, the super elastic nature of the distally disposed hoop (not shown) provides the self-expanding property. The distal end 24 of the expandable member 20 may include a polymer coating or covering to form an atraumatic tip.

Figure 2:
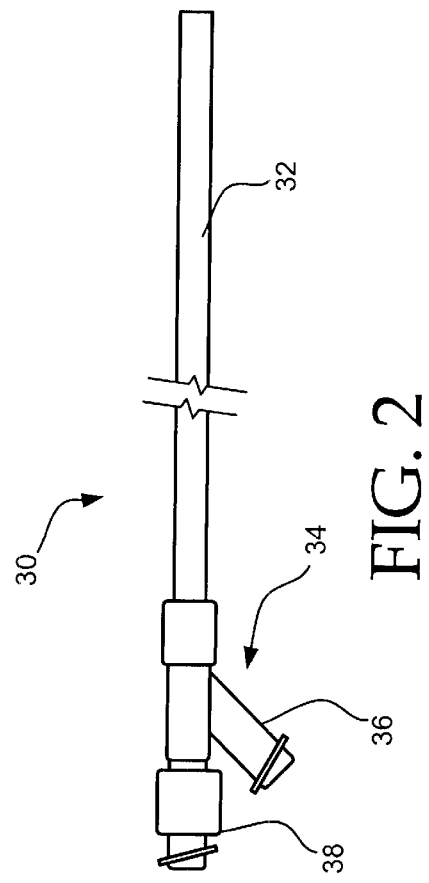
FIG. 2 is a schematic illustration of a sheath for use in combination with the stent positioning device illustrated in FIG. 1.

Refer now to FIG. 2 which illustrates a sheath 30 for use in combination with the stent positioning device 10 illustrated in FIG. 1. The sheath 30 includes an elongate shaft 32 having a proximal end, a distal end, and a lumen (not shown) extending therethrough. The proximal end of the elongate shaft 32 is connected to a manifold 34 having a sidearm 36 and a rotational hemostasis valve 38, which are substantially the same as the corresponding elements described with reference to manifold 14 illustrated in FIG. 1. The distal end of the elongate shaft 32 may include a radiopaque marker band (not shown) to facilitate radiographic visualization. The sheath 30 may otherwise have a conventional catheter design.

Figure 3A:
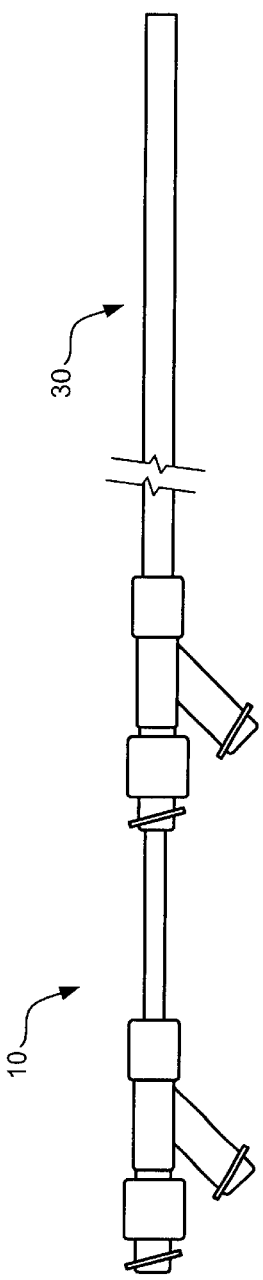
FIGS. 3A–3C are schematic illustrations of the stent positioning device and sheath as shown in FIGS. 1 and 2, respectively, demonstrating the expansion/collapse of the expandable member.
Figure 3B:
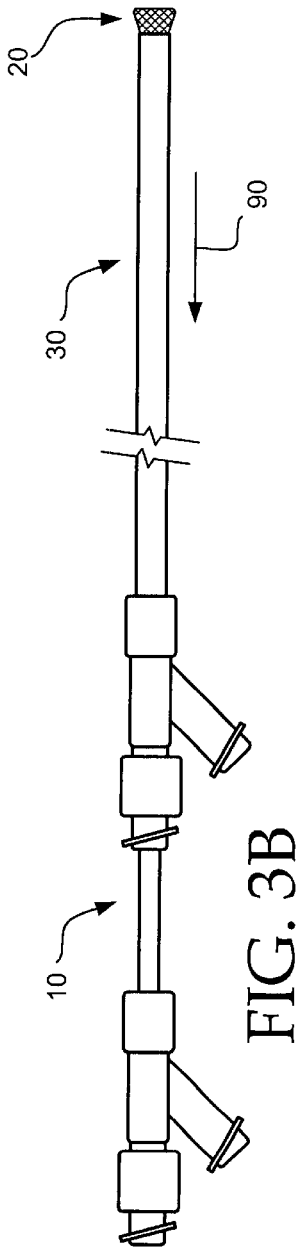
Figure 3C:
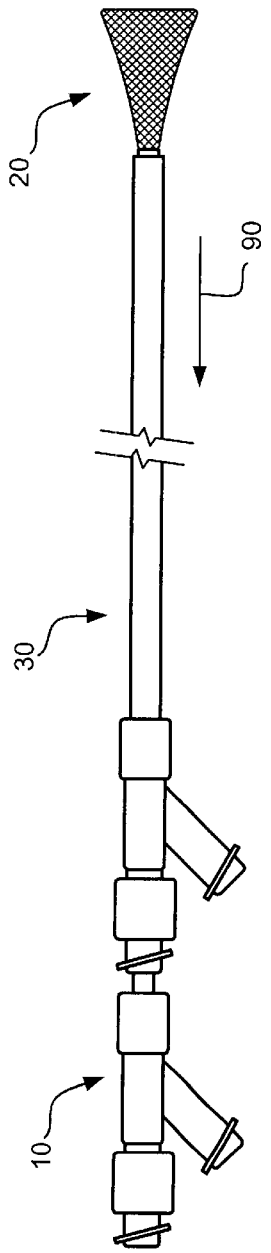

The sheath 30 is slidably disposed about the stent positioning device 10 as illustrated in FIGS. 3A–3C. The sheath 30 is slidable relative to the stent positioning device 10 between an advanced position as illustrated in FIG. 3A and a retracted position as illustrated in FIG. 3C. In the advanced position, the sheath 30 covers the elongate shaft 12 and the expandable member 20 of the stent positioning device 10. In this position, the sheath 30 constrains the expandable member 20 to facilitate insertion and navigation of the stent positioning device 10 through the patient's vasculature. The sheath 30 may be retracted in the proximal direction as indicated by arrow 90 in FIG. 3B to gradually allow expansion of the expandable member 20. As the sheath 30 is retracted further in the proximal direction as indicated by arrow 90 to the fully retracted position as illustrated in FIG. 3C, full expansion and deployment of the expandable member 20 is achieved. The sequence of these steps may be reversed to facilitate collapse of the expandable member 20 and removal of the stent positioning device 10.

As an alternative, the guide catheter 80, as discussed hereinafter with reference to FIG. 4, may be used in place of sheath 30 to facilitate expansion and collapse of the expandable member 20. In particular, the guide catheter 80 may be advanced or retracted over the stent positioning device 10 to selectively allow expansion or collapse of the expandable member 20.

Figure 4:
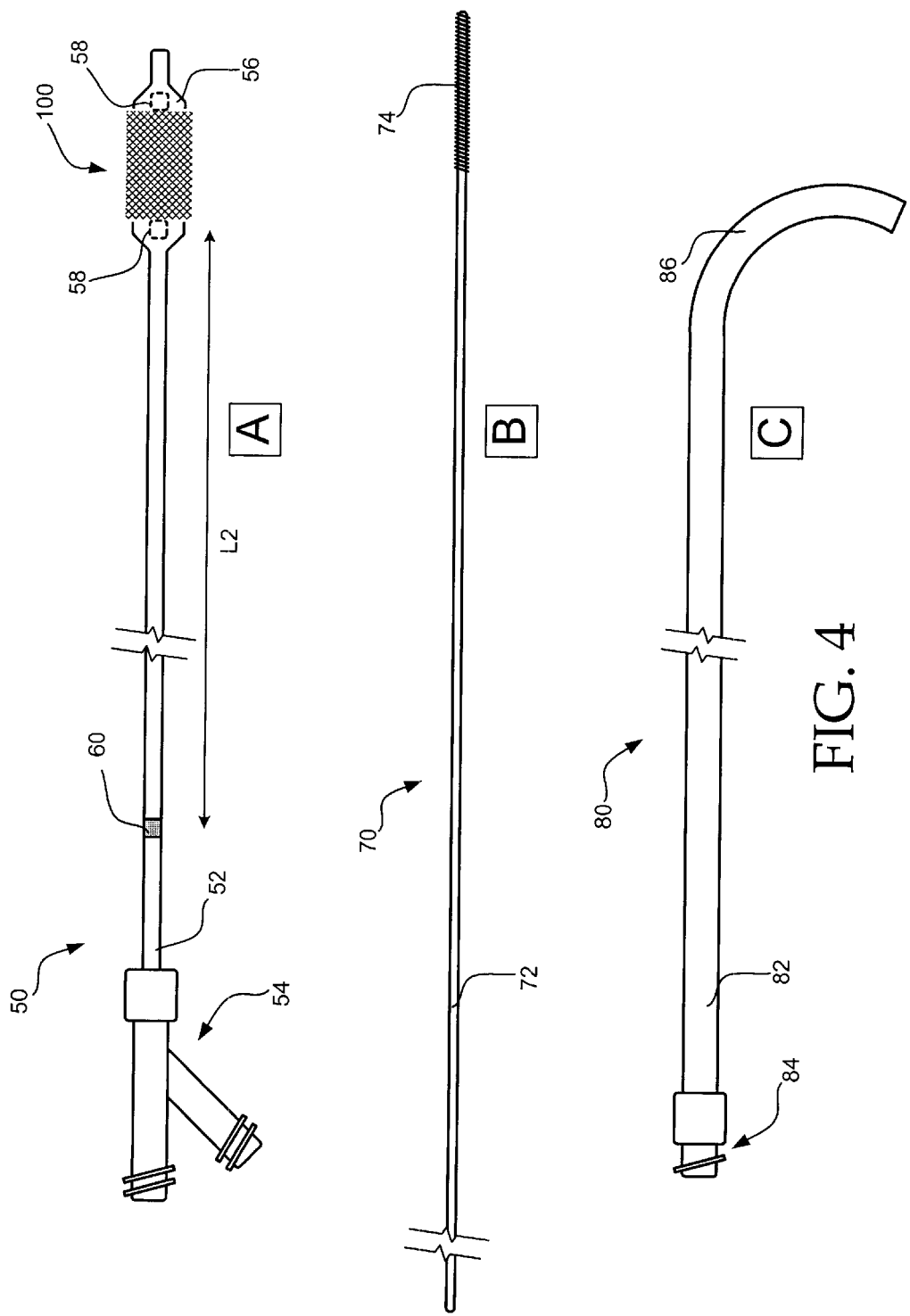
FIG. 4 is a schematic illustration of a substantially conventional stent delivery catheter, conventional guidewire and conventional guide catheter.

To facilitate further discussion of the stent positioning device 10 and its use, refer now to FIG. 4 which schematically illustrates a substantially conventional stent delivery catheter 50, a conventional guidewire 70 and a conventional guide catheter 80. The stent delivery catheter 50, the guidewire 70 and the guide catheter 80 may comprise substantially conventional devices for coronary or peripheral intravascular applications.

The stent delivery catheter 50 includes an elongate shaft 52 having a proximal end, a distal end, a guide wire lumen and an inflation lumen extending therethrough. A manifold 54 is connected to the proximal end of the shaft 52 and a balloon 56 is connected to the distal end of the shaft 52. A conventional intravascular stent 100 is disposed about the balloon 56. The intravascular stent 100 may be self-expanding or balloon-expandable. Although not shown, the stent delivery catheter 50 may include a retractable sheath to facilitate deployment of the stent 100, particularly if the stent 100 is self-expanding. In addition, those skilled in the art will recognize that the stent delivery catheter 50 may be used without a balloon 56 depending on the type of intravascular stent 100 being delivered.

As illustrated, the balloon 56 is inflated and the stent 100 is expanded/deployed. However, during insertion and navigation, the balloon 56 is deflated and the stent 100 is collapsed thereon. Radiopaque marker bands 58 are provided on the elongate shaft 52 under the balloon 56 to facilitate radiographic placement of the proximal and distal ends of the stent 100. A proximal marker 60 is provided on the proximal end of the elongate shaft 52. The proximal marker 60 remains outside the patient's body and guide catheter 80 such that it is readily visible to the treating physician. The proximal marker 60 is positioned at a length L2 from the proximal end of the stent 100 (adjacent the proximal radiopaque marker 58) that is equal to the overall length L1 of the stent positioning device 10. The stent delivery catheter 50 comprises a conventional balloon stent delivery catheter with the exception of the proximal marker 60.

The elongate shaft 52 of the stent delivery catheter 50 preferably has an outside diameter that closely corresponds to the inside diameter of the elongate shaft 12 of the stent positioning device 10 to provide a snug fit therebetween and to minimize slack when the stent delivery catheter 50 and stent positioning device 10 are subject to intravascular curvature. By providing a snug fit and minimizing slack, the accurate correlation between L1 and L2 may be maintained.

Preferably, the overall length L1 of the stent positioning device 10 is approximately 3 cm shorter than the stent delivery catheter 50. Assuming the expandable member 20 has a preferable length of approximately 1 cm, the overall length of the sheath 30 is preferably approximately 1.5 cm shorter than the overall length of the stent positioning device 10.

The conventional guidewire 70 includes an elongate shaft 72 which typically comprises a stainless steel wire. The guidewire 70 also includes a distally disposed radiopaque coil 74 to facilitate atraumatic intravascular navigation and radiographic visualization.

The conventional guide catheter 80 includes an elongate shaft 82 having a lumen (not shown) extending therethrough. The distal end of the elongate shaft 82 includes a curve 86 which may comprise a wide variety of shapes depending on the particular anatomy being navigated. The proximal end of the elongate shaft 82 is connected to a conventional manifold 84 to facilitate flushing of the lumen in the shaft 82. At least the distal tip of the elongate shaft 82 is radiopaque to facilitate radiographic visualization.

In use, the guide catheter 80 and guidewire 70 will typically be inserted into the patient's vascular system during a prior angioplasty or atherectomy procedure. In particular, the distal end of the guide catheter 80 will be positioned in the ostium of the vascular lumen to be treated. The proximal end of the guide catheter will extend outside the patient's body. The guidewire 70 will extend through the guide catheter 80 and across the treatment site within the vascular lumen.

If necessary, the intravascular stent 100 is placed on the balloon 56 of the stent delivery catheter 50. However, it is anticipated that the stent 100 will be placed on the balloon 56 by the manufacture of the stent delivery catheter 50. The stent positioning device 10 is then placed on the stent delivery catheter 50 by sliding the proximal end of the stent positioning device 10 over the distal end of the stent delivery catheter 50. If the sheath 30 is to be used to selectively deploy the expandable member 20, the sheath 30 is positioned on the stent positioning device 10 as illustrated in FIG. 3A. If the guide catheter 80 is to be used to facilitate selective expansion of the expandable member 20, the expandable member 20 may be collapsed using a peel-away sheath to facilitate insertion of the stent positioning device 10 into the manifold 84 of the guide catheter 80.

With the intravascular stent 100 and stent positioning device 10 disposed on the stent delivery catheter 50, the stent delivery catheter 50 is inserted into the patient's vasculature over the guidewire 70 and through the guide catheter 80. The stent delivery catheter 50 is navigated through the patient's vasculature until the stent 100 is disposed distal of the desired treatment site and the distal end 24 of the expandable member 20 is proximal of the ostium. If necessary, the stent positioning device 10 may be repositioned, while the stent delivery catheter 50 and guidewire 70 remain in place, such that the distal end 24 of the expandable member 20 is proximal of the ostium. Since the distal end of the guide catheter 80 is seated in the ostium, the guide catheter 80 must also be retracted in the proximal direction until the distal end thereof is approximately 1 cm proximal of the ostium. These steps may be confirmed utilizing radiographic and fluoroscopic visualization techniques.

With the distal end 24 of the expandable member 20 disposed proximal of the ostium, the expandable member 20 may be expanded by retracting the sheath 30 in the proximal direction as illustrated in FIGS. 3A–3C. Alternatively, if the guide catheter 80 is used in placed of sheath 30, the guide catheter 80 may be retracted in the proximal direction to allow expansion of the expandable member 20. Once the expandable member 20 is fully expanded, the stent positioning device 10 is advanced in the distal direction until the distal end 24 of the expandable member 20 engages the ostium.

The stent delivery catheter 50 is then retracted in the proximal direction, while the stent positioning device 10 remains in place, until the proximal end of the stent 100 is positioned adjacent the distal end 24 of the expandable member 20. This may be confirmed by positioning the proximal visible marker 60 adjacent the proximal end of the stent positioning device 10. Alternatively, this may be confirmed utilizing radiographic visualization techniques assuming the distal end of the expandable member 20 and the intravascular stent 100 are radiopaque.

With the proximal end of the stent 100 positioned adjacent to the distal end 24 of the expandable member 20, the stent 100 may then be deployed utilizing conventional techniques. After the stent 100 has been successfully deployed in the vascular lumen adjacent to the ostium, the sheath 30 or guide catheter 80 may be advanced in the distal direction to collapse the expandable member 20. After the expandable member 20 has been collapsed, the stent positioning device 10 and stent delivery catheter 50 may be retracted through the guide catheter 80 and removed from the patient's vasculature. The guidewire 70 and guide catheter 80 may then be removed from the patient's vasculature to complete the procedure.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular system for delivering a stent to a vascular lumen adjacent an ostium, comprising:

a stent delivery catheter having a proximal end, a proximal portion and a distal portion;

a stent disposed about the distal portion of the stent delivery catheter, the stent having a proximal end and a distal end; and a stent positioning device disposed about the stent delivery catheter, the stent positioning device having a proximal end, a distal end, a length (L1), and a distally disposed expandable member, the expandable member having a distal expanded diameter that is larger than the vascular lumen adjacent the ostium.

2. An intravascular system of claim 1, wherein the stent delivery catheter includes a visible marker disposed on the proximal portion thereof, and wherein the visible marker and the proximal end of the stent are separated by a length (L2) equal to the length (L1) of the stent positioning device such that the proximal end of the stent may be positioned in the vascular lumen adjacent the ostium when the proximal end of stent positioning device is positioned at the visible marker and the distal end of the expandable member engages the ostium.

3. An intravascular system of claim 2, wherein a close fit is provided between the stent delivery catheter and the stent positioning device such that L1 remains equal to L2 despite curvature of the stent delivery catheter and stent positioning device.

4. An intravascular system of claim 1, wherein the distal end of the expandable member is radiopaque such that the proximal end of the stent may be located in the vascular lumen adjacent the ostium when the proximal end of stent is positioned at the distal end of the expandable member and the distal end of the expandable member engages the ostium.

5. An intravascular system of claim 1, wherein the expandable member includes perfusion apertures to allow blood perfusion across the ostium and into the vascular lumen.

6. An intravascular system of claim 5, wherein the expandable member comprises a radially resilient but longitudinally rigid structure.

7. An intravascular system of claim 5, wherein the expandable member comprises a self-expanding structure.

8. An intravascular system of claim 7, wherein the structure comprises a tubular braid or mesh.

9. An intravascular system of claim 7, wherein the self-expanding structure comprises a super elastic material.

10. An intravascular system of claim 9, wherein the super elastic material comprises a nickel titanium alloy.

11. An intravascular system of claim 7, wherein the expandable structure includes a distal hoop.

12. An intravascular system of claim 11, wherein the hoop comprises a super elastic material.

13. An intravascular system of claim 7, wherein the distal end of the expandable member includes an atraumatic tip.

14. An intravascular system of claim 13, wherein the atraumatic tip comprises a polymer.

15. An intravascular system of claim 7, further comprising a sheath disposed about the stent positioning device.

16. An intravascular system of claim 15, wherein the sheath is movable between a retracted position and an advanced position.

17. An intravascular system of claim 16, wherein the expandable member is expanded when the sheath is in the retracted position and the expandable member is collapsed when the sheath is in the advanced position.

18. A method of delivering a stent through a patients vasculature to a vascular lumen adjacent an ostium, comprising the steps of:
providing a stent delivery catheter having a proximal portion, a distal portion and a distally disposed stent;
providing a stent positioning device having a proximal end, a distal end, and a distally disposed expandable member, the expandable member having a distal end and a distal expanded diameter that is larger than the vascular lumen adjacent the ostium;
placing the stent positioning device about the stent delivery catheter;
inserting and navigating the stent delivery catheter and stent positioning device through the vasculature to the vascular lumen across the ostium;
expanding the expandable member;
advancing the stent positioning device until the distal end of the expandable member engages the ostium;
retracting the stent delivery catheter while the stent positioning device remains in place until the proximal end of the stent is positioned adjacent the distal end of the expandable member; and
deploying the stent such that the proximal end of the stent is located in the vascular lumen adjacent the ostium.

19. A method of claim 18, wherein the proximal portion of the stent delivery catheter includes a visible marker separated from a proximal end of the stent by a length equal to the length of the stent positioning device, and wherein the stent delivery catheter is retracted until the proximal end of stent positioning device is positioned at the visible marker.

20. An method of claim 18, wherein the distal end of the expandable member is radiopaque, and wherein the stent delivery catheter is retracted until the proximal end of stent is positioned at the distal end of the expandable member utilizing radiographic visualization.

21. An method of claim 18, further comprising the steps of:
collapsing the expandable member; and
withdrawing the stent delivery catheter and stent positioning device from the patient's vasculature.

22. A method of claim 18, further comprising the steps of:
providing a sheath disposed about the stent positioning device and the expandable member; and
moving the sheath relative to the expandable member to expand or collapse the expandable member.

23. A method of claim 18, further comprising the steps of:
providing a guide catheter disposed about the stent positioning device and the expandable member; and
moving the guide catheter relative to the expandable member to expand or collapse the expandable member.

24. A method of delivering a stent through a patient's vasculature to a vascular lumen adjacent an ostium utilizing a stent delivery catheter having the stent distally disposed thereon and a stent positioning device having an expandable member, the method comprising the steps of:
positioning the stent positioning device in the vasculature such that a distal end of the expandable member engages the ostium;
positioning the stent delivery catheter such that a proximal end of the stent is positioned adjacent the distal end of the expandable member; and
deploying the stent such that the proximal end of the stent is located in the vascular lumen adjacent the ostium.

25. A method of claim 24, wherein the stent positioning device has a length L1, wherein the stent delivery catheter includes a visible marker separated from the proximal end of the stent by a length L2 equal to L1, and wherein the stent is deployed when the proximal end of stent positioning device is positioned at the visible marker.

26. A method of claim 24, wherein the distal end of the expandable member is radiopaque and wherein the stent is deployed when the proximal end of the stent is positioned at the distal end of the expandable member using radiographic visualization.

* * * * *